(12) United States Patent
Nordberg

(10) Patent No.: US 7,691,875 B2
(45) Date of Patent: *Apr. 6, 2010

(54) IMIDAZOPYRIDINE COMPOUNDS, PROCESSES FOR THEIR PREPARATION AND THERAPEUTIC USES THEREOF

(75) Inventor: Peter Nordberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 932 days.

This patent is subject to a terminal disclaimer.

(21) Appl. No.: 10/561,199

(22) PCT Filed: Jun. 23, 2004

(86) PCT No.: PCT/SE2004/001013

§ 371 (c)(1),
(2), (4) Date: Dec. 19, 2005

(87) PCT Pub. No.: WO2004/113339

PCT Pub. Date: Dec. 29, 2004

(65) Prior Publication Data

US 2007/0066642 A1    Mar. 22, 2007

(30) Foreign Application Priority Data

Jun. 26, 2003   (SE) ................................. 0301904

(51) Int. Cl.
*A61K 31/437*   (2006.01)
*C07D 471/04*   (2006.01)

(52) U.S. Cl. ....................... 514/300; 546/121

(58) Field of Classification Search ....................... None
See application file for complete search history.

(56) References Cited

U.S. PATENT DOCUMENTS

| 4,450,164 | A | 5/1984 | Bristol et al. | |
| 4,725,601 | A | 2/1988 | Ueda et al. | |
| 6,313,136 | B1 * | 11/2001 | Amin et al. | 514/300 |
| 6,313,137 | B1 * | 11/2001 | Amin et al. | 514/300 |

FOREIGN PATENT DOCUMENTS

| EP | 033094 B1 | 8/1981 |
| EP | 204285 B1 | 12/1986 |
| WO | WO 99/55705 A1 | 11/1999 |
| WO | WO 99/55706 A1 | 11/1999 |
| WO | WO 00/11000 A2 | 3/2000 |
| WO | WO 02/064118 A1 | 8/2002 |
| WO | WO 03/018582 A1 | 3/2003 |

OTHER PUBLICATIONS

Kaminski et al., "Antiulcer Agents. 1. Gastric Antisecretory and Cytoprotective Properties of Substituted Imidazo[1,2-a]pyridines"; J. Med. Chem., vol. 28, 876-892, (1985).

Kaminski et al., "Antiulcer Agents. 2. Gastric Antisecretory, Cytoprotective, and Metabolic Properties of Substituted Imidazo[1,2-a]pyridines and Analogues"; J. Med. Chem., vol. 30, 2031-2046, (1987).

Kaminski et al., "Antiulcer Agents. 3. Structure-Activity-Toxicity Relationships of Substituted Imidazo[1,2-a]pyridines and a Related Imidazo[1,2-a]pyrazine"; J. Med. Chem., vol. 30, 2047-2051, (1987).

Kaminski et al., "Antiulcer Agents. 4. Conformational Considerations and the Antiulcer Activity of Substituted Imidazo[1,2-a]pyridines and Related Analogues"; J. Med. Chem., vol. 32, 1686-1700, (1989).

Kaminski et al., "Antiulcer Agents. 5. Inhibition of Gastric $H^+/K^+$—ATPase by Substituted Imidazo[1,2-a]pyridines and Related Analogues and Its Implication in Modeling the High Affinity Potassium Ion Binding Site of the Gastric Proton Pump Enzyme"; J. Med. Chem., vol. 34, 533-541, (1991).

Sachs et al., "The Pharmacology of the Gastric Acid Pump: The $H^+/K^+$—ATPase"; Annu. Rev. Pharmacol. Toxicol. 35: 277-305, (1995).

Berglindh et al., "Effects of Secretagogues on Oxygen Consumption, Aminopyrine Accumulation and Morphology in Isolated Gastric Glands"; Acta Physiol. Scand. 97: 401-414, (1976).

LeBel et al., "A Convenient Method for the ATPase Assay"; Anal. Biochem., 85, 86-89, (1978).

Popovic et al., "Permanent Cannulation of Aorta and Vena Cava in Rats and Ground Squirrels"; J. Appl. Physiol., 15, 727-728, (1960).

* cited by examiner

*Primary Examiner*—Phyllis G. Spivack
(74) *Attorney, Agent, or Firm*—White & Case LLP

(57) ABSTRACT

The present invention relates to imidazopyridine derivatives of the Formula I and, therapeutically acceptable salts thereof which inhibit exogenously or endogenously stimulated gastric acid secretion and thus can be used in the treatment of gastrointestinal inflammatory diseases. In further aspects, the invention relates to the compound of the invention for use in therapy; to processes for preparation of such new compound; to pharmaceutical compositions containing the compound of the invention, or a therapeutically acceptable salt thereof, as active ingredient; and to the use of the compound of the invention in the manufacture of medicaments for the medical use indicated above.

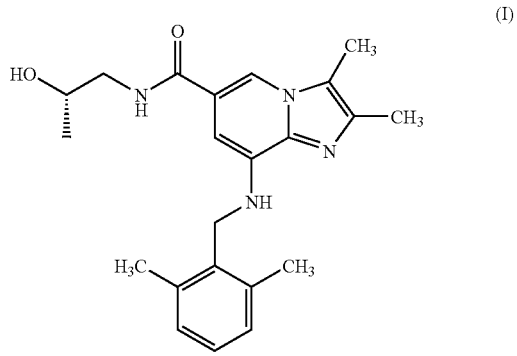

(I)

4 Claims, No Drawings

IMIDAZOPYRIDINE COMPOUNDS, PROCESSES FOR THEIR PREPARATION AND THERAPEUTIC USES THEREOF

TECHNICAL FIELD

The present invention relates to a novel compound, and therapeutically acceptable salts thereof, which inhibit exogenously or endogenously stimulated gastric acid secretion and thus can be used in the treatment of gastrointestinal inflammatory diseases. In further aspects, the invention relates to the compound of the invention for use in therapy; to processes for preparation of such new compound; to pharmaceutical compositions containing the compound of the invention, or a therapeutically acceptable salt thereof, as active ingredient; and to the use of the compound of the invention in the manufacture of medicaments for the medical use indicated above.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); from WO99/55706 and WO99/55705 (AstraZeneca); from WO 03/018582 (AstraZeneca); and from publications by J. J. Kaminski et al. in the Journal of Medical Chemistry (vol. 28, 876-892, 1985; vol. 30, 2031-2046, 1987; vol. 30, 2047-2051, 1987; vol. 32, 1686-1700, 1989; and vol. 34, 533-541, 1991).

For a review of the pharmacology of the gastric acid pump (the $H^+$, $K^+$-ATPase), see Sachs et al. (1995) Annu. Rev. Pharmacol. Toxicol. 35: 277-305.

We have now found a substituted imidazo[1,2-a]pyridine, useful in the treatment of peptic ulcer diseases exhibiting advantageous properties e.g. fast onset, high potency and/or long duration, high solubility and high dissolution rate.

DISCLOSURE OF THE INVENTION

It has surprisingly been found that compound of the Formula I is particularly effective as inhibitor of the gastrointestinal $H^+$, $K^+$-ATPase and thereby as inhibitor of gastric acid secretion.

In one aspect, the present invention thus relates to a compound of Formula I

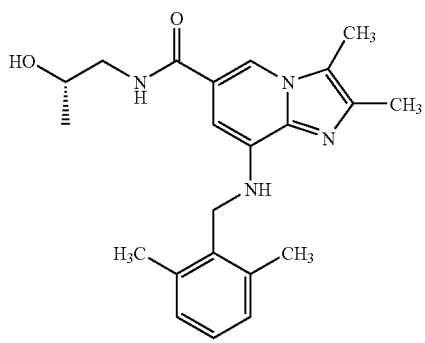

I or a pharmaceutically acceptable salt thereof.

Depending on the process conditions the end product of the Formula I is obtained either in neutral or salt form. Both the free base and the salts of the end product are within the scope of the invention.

In the preparation of acid addition salts, preferably such acids are used which form therapeutically acceptable salts. Examples of such acids are hydrohalogen acids such as hydrochloric acid, sulphuric acid, phosphoric acid, nitric acid, aliphatic, alicyclic, aromatic or heterocyclic carboxyl or sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulphonic acid, ethanesulphonic acid, hydroxyethanesulphonic acid, halogenbensenesulphonic acid, toluenesulphonic acid or naphthalenesulphonic acid.

Preparation

The present invention also provides the following process for the manufacture of the compound with Formula I.

A process for manufacture of compound with Formula I comprises the following steps:

a) compound of Formula II

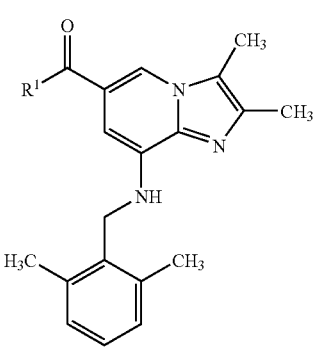

II wherein $R^1$ represents a $C_1$-$C_6$-alkoxygroup or —NH2, can be hydrolyzed under standard conditions in the presence of an aqueous acid or a base, to the corresponding carboxylic acid compound of Formula III

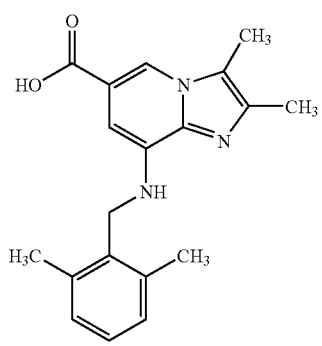

III

The acid and base can be selected from HCl, $H_2SO_4$ and NaOH.

b) compound of the Formula m can be reacted with amino compound of Formula IV

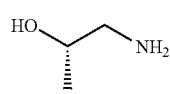

IV in the presence of a coupling reagent, such as o-benzotriazol-1-yl-N,N,N',N'-tetramethyluronium tetrafluoroborate (TBTU) to the corresponding amide, i.e. the compound of Formula I. The reaction can be carried out in an inert solvent, such as dimethyl formamide (DM), methylenchloride and acetonitrile, or mixture thereof, under standard conditions.

In one embodiment of the invention, the reaction according to step a) above can be carried out by hydrolyzing a compound of Formula II to the corresponding acid in the presence of NaOH in an aqueous alcohol, such as aqueous methanol or ethanol, at reflux for 1 to 3 hours.

A further process for producing the compound of the invention comprises the following step a) compound of Formula V,

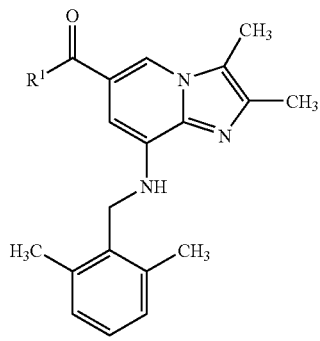

V wherein $R^1$ represents a $C_1$-$C_6$-alkoxy group, can be reacted with an amino compound of Formula IV

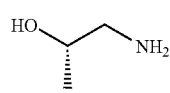

IV to give the corresponding amide, i.e. the compound of Formula I.

The reaction can be carried out by heating the reactants in the neat amino compound or dissolved in an inert solvent under standard conditions, e.g. in an alcohol such as methanol, at elevated temperature, such as between 40 to 60° C., or at reflux. The reaction can be performed in the presence of a base or a cyanide salt.

In one embodiment of the present invention the reaction is performed in the presence of a base selected from 1,8-diacabicyclo(5.4.0)undec-7-ene (DBU) or 1,5-diazabicyclo(4.3.0)non-5-ene (DBN).

In a further embodiment of the present invention, the reaction is performed in the presence of an alkoxide, such as sodium methoxide, potassium methoxide, or potassium ethoxide.

In one embodiment of the invention the compound of Formula V is mixed with the compound of Formula IV in a solvent, such as an alcohol, for example methanol or ethanol. The base is added to the heated reaction mixture and the reaction is completed at an elevated temperature, for example between 40 to 60° C., or at reflux. The base can be selected from, among others, potassium methoxide, or sodium methoxide.

Medical Use

In a further aspect, the invention relates to the compound of Formula I for use in therapy. In particular, the invention provides the use of a compound of Formula I in the manufacture of a medicament for the inhibition of gastric acid secretion, or for the treatment of gastrointestinal inflammatory diseases.

The compound according to the invention may thus be used for treatment of gastrointestinal inflammatory diseases, and gastric acid-related diseases in mammals including man, such as gastritis, reflux esophagitis, Zollinger-Ellison syndrome and peptic ulcer disease including gastric ulcer and duodenal ulcer. Furthermore, the compound may be used for treatment of other gastrointestinal disorders where gastric antisecretory effect is desirable, e.g. in patients with gastrinomas, and in patients with acute upper gastrointestinal bleeding. The compound may also be used for effective control and treatment of heartburn and other Gastroesophageal Reflux Disease (GERD) symptoms (acute and maintenance symptomatic GERD, erosive esophagitis healing and maintenance), regurgitation, short and long-term management of acid reflux disease and nausea. They may also be used in patients in intensive care situations, and pre-and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance, preferably in the range of 20 to 60 mg, for instance 50 mg. The compound of the invention may be administered to the patient in a continuous treatment as well as on-demand treatment, depending on the individual requirements and the disease. By the compound of the invention possibilities to improve the quality of life for the individuals suffering from gastric acid related diseases and/or gastrointestinal inflammatory diseases are given.

Pharmaceutical Formulations

In yet a further aspect, the invention relates to pharmaceutical compositions containing the compound of the invention, or a therapeutically acceptable salt thereof, as active ingredient.

For clinical use, the compound of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of the compound of the invention is between 0.1-95% by weight of the preparation, preferably between 0.1-20% by weight in preparations for parenteral use and preferably between 0.1-50% by weight in preparations for oral administration.

In the preparation of pharmaceutical formulations containing a compound of the invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing the active compound of the invention, vegetable oil, fat, or other suitable vehicle for soft gelatin capsules. Hard gelatin capsules may contain granules of the compound of the invention. Hard gelatin capsules may also contain the compound of the invention in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound of the invention mixed with a neutral fat base; (ii) in the form of a gelatin rectal capsule which contains the compound of the invention in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the compound of the invention and the remainder consisting of sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compound according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:
- β-lactam antibiotics such as amoxicillin, ampicillin, cephalothin, cefaclor or cefixime;
- macrolides such as erythromycin, or clarithromycin;
- tetracyclines such as tetracycline or doxycycline;
- aminoglycosides such as gentamycin, kanamycin or amikacin;
- quinolones such as norfloxacin, ciprofloxacin or enoxacin;
- others such as metronidazole, nitrofurantoin or chloramphenicol; or
- preparations containing bismuth salts such as bismuth subcitrate, bismuth subsalicylate, bismuth subcarbonate, bismuth subnitrate or bismuth subgallate.

The compound according to the invention can also be used together or in combination for simultaneous, separate or sequential use with antacids such as aluminium hydroxide, magnesium carbonate and magnesium hydroxide or alginic acid, or together or in combination for simultaneous, separate or sequential use with pharmaceuticals which inhibit acid secretion, such as, $H_2$-blockers (e.g. cimetidine, ranitidine), $H^+$, $K^+$-ATPase inhibitors (e.g. omeprazole, pantoprazole, lansoprazole or rabeprazole), or together or in combination for simultaneous, separate or sequential use with gastroprokinetics (e.g. cisapride or mosapride).

The compound according to the invention can also be used together or in combination for simultaneous, separate or sequential use with other active ingredients, e.g. for the treatment of conditions involving medicament induced gastric ulcer. Such other active ingredients may be a NSAID, a NO-releasing NSAID, a COX-2 inhibitor or a bisphosphonate.

The compound according to the invention can also be used together or in combination for simultaneous, separate or sequential use with a gastrin antagonist such as a CCK2 antagonist.

Intermediates

A further aspect of the invention is a new intermediate compound which is useful in the synthesis of the compound according to the invention.

Thus, the invention includes compound of Formula III

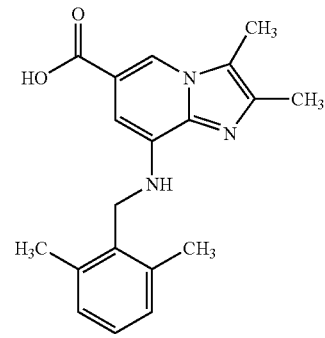

EXAMPLES

1. Preparation of the Compound of the Invention

Example 1

Synthesis of 8-[(2,6-dimethylbenzyl)amino]-2,3-dimethylimidazo[1,2-a]pyridine-6-carboxylic acid

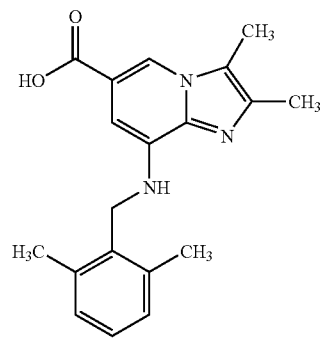

8-Isopropyl [(2,6-dimethylbenzyl)amino]-2,3-dimethylimidazo[1,2-a]pyridine-6-carboxylate (100 g, 0.274 mol) was added to methanol (900 ml) and water (100 ml).

Sodium hydroxide (45 g, 1.13 mol) was added and the mixture was refluxed for 2 h. About half of the solvent was evaporated and the product was precipitated by adding acetic acid (100 ml) and water (1000 ml). The mixture was stirred over night at room temperature. The product was filtered off and washed with water and acetone. 88 g (99%) of the compound of the invention was obtained.

1H NMR (DMSO, 400 Mz) δ 2.22 (s, 3H), 2.33 (s, 6H), 2.36 (s, 3H), 4.36 (d, 2H), 5.03 (t, 1H), 6.64 (s, 1H), 7.04-7.15 (m, 3H), 8.05 (s, 1H).

Example 2

8-[(2,6-dimethylbenzyl)amino]-N-[(2S)-2-hydroxypropyl]-2,3-dimethylimidazo[1,2-a]pyridine-6-carboxamide

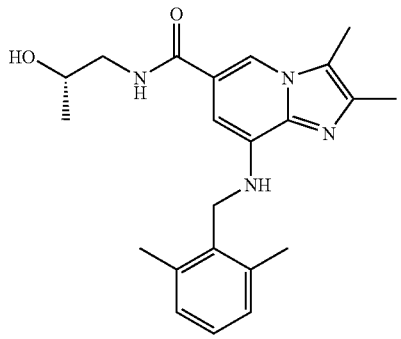

8-[(2,6-dimethylbenzyl)amino]-2,3-dimethylimidazo[1,2-a]pyridine-6-carboxylic acid (30 g, 0.0928 mol) and 30 g diisopropylethylamine (30 g, 0.233 mol) were added to dimethylformamide (DM) (250 ml). o-benzotriazol-1-yl-N,N,N',N'-tetramethyluronium tetrafluoroborate (TBTU) (36 g, 0.112 mol) was added. The mixture was stirred for 15 min at room temperature. (S)-1-amino-2-propanol (8.4 g, 0.112 mol) was added and the stirring was continued for 1 h at room temperature. Water (100 ml) was added and the reaction mixture was heated to 70° C. The product was precipitated by slowly adding more water (200 ml). The mixture was then stirred for 5 h at 65-70° C. After cooling to room temperature the product was filtered off and washed with 40% methanol solution. 33.7 g of the compound of the invention was obtained.

1H NMR (CDCl3, 300 MHz) δ 1.20 (d, 3H), 2.29 (s, 3H), 2.32 (s, 3H), 2.35 (s, 6H), 3.12-3.21 (m, 1H), 3.58-3.66 (m, 2H), 3.96 4.06 (m, 1H), 4.29 (d, 2H), 5.00 (t, 1H), 6.41 (s, 1H), 6.89 (t, 1H), 7.02-7.15 (m, 3H), 7.71 (s, 1H).

Example 3

8-[(2,6-dimethylbenyl)amino]-N-[(2S)-2-hydroxypropyl]-2,3-dimethylimidazo[1,2-a]pyridine-6-carboxamide mesylate salt

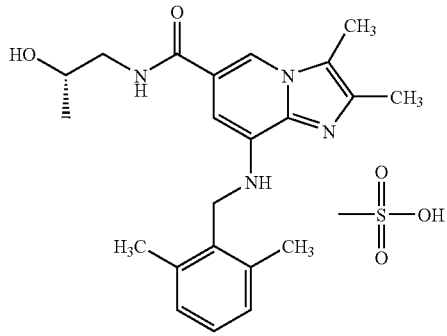

8-[(2,6-dimethylbenzyl)amino]-N-[(2S)-2-hydroxypropyl]-2,3-dimethylimidazo[1,2-a]pyridine-6-carboxamide (29.0 g, 0.0762 mol) was dissolved in refluxing isopropanol (280 ml). Methanesulfonic acid (7.4 g, 0.0770 mol), dissolved in isopropanol (20 ml), was added to the solution. When cooled, a crystalline substance precipitated. The mixture was left over night at room temperature. The product was filtered off and washed with isopropanol. 29.9 g of the compound of the invention as mesylate salt was obtained.

1H NMR (DMSO, 500 MHz) δ 1.10 (d, 3H), 2.25 (s, 3H), 2.36 (s, 6H), 2.42 (s, 3H), 2.48 (s, 3H), 3.21-3.33 (m, 2H), 3.82-3.85 (m, 1H), 4.42 (d, 2H), 6.16 (s, 1H), 7.13-7.21 (m, 3H), 7.36 (s, 1H), 8.42 (s, 1H) 8.79 (t, 1H) 13.68 (bs, 1H).

Example 4

8-[(2,6-dimethylbenzyl)amino]-N-[(2S)-2-hydroxypropyl]-2,3-dimethylimidazo[1,2-a]pyridine-6-carboxamide

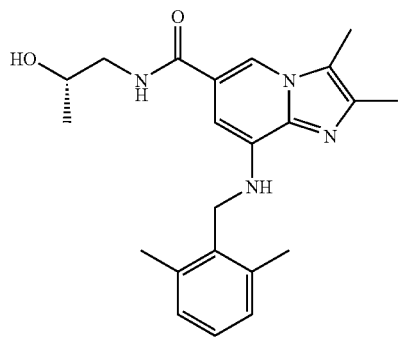

A mixture of 8-isopropyl-[(2,6-dimethylbenzyl)amino]-2,3-dimethylimidazo[1,2-a]pyridine-6-carboxylate (5 g, 13 mmol) and (S)-1-amino-2-propanol (3.8 g, 50 mmol) in methanol (10 ml) and toluene (10 ml) was heated to 40-45° C. Potassium methoxide (0.57 g, 2.6 mmol) was added as a solution in methanol (32% w/w). The reaction mixture was heated to reflux (67-68° C.) and kept at this temperature until desired conversion (2-4 h) checked with HPLC.

After cooling and charging of water (15 ml) the product precipitated. The product was filtered off, washed with water, and dried under vacuum. 4.1 g (80%) of the compound of the invention was obtained as a white solid.

Biological Tests

Biological tests of the compound according to the invention have been performed as described below. The tests have also been performed with 8-[(2,6-dimethylbenzyl)amino]-N-(2-hydroxyethyl)-2,3-dimethylimidazo[1,2-a]pyridine-6-carboxamide as a reference compound. 8-[(2,6-dimethylbenzyl)amino]-N-(2-hydroxyethyl)-2,3-dimethylimidazo[1,2-a]pyridine-6-carboxamide is specifically disclosed in WO 99/55705.

1. In vitro Experiments

Acid Secretion Inhibition in Isolated Rabbit Gastric Glands

Inhibiting effect on acid secretion in vitro in isolated rabbit gastric glands was measured as described by Berglindh et al. (1976) Acta Physiol. Scand. 97, 401-414.

The inhibitory value for the compound of the invention was determined, , $IC_{50}$, to 0.26 µmol/l. The $IC_{50}$ for 8-[(2,6-dimethylbenzyl)amino]-N-(2-hydroxyethyl)-2,3-dimethylimidazo[1,2-a]pyridine-6-carboxamide was measured to 0.28 µmol/l.

Determination of $H^+,K^+$-ATPase Activity

Membrane vesicles (2.5 to 5 µg) were incubated for 15 min at +37° C. in 18 mM Pipes/Tris buffer pH 7.4 containing 2 mM $MgCl_2$, 10 mM KCl and 2 mM ATP. The ATPase activity was estimated as release of inorganic phosphate from ATP, as described by LeBel et al. (1978) Anal. Biochem. 85, 86-89.

The inhibitory value, $IC_{50}$, of the compound of the invention was measured 0.69 µmol/l. The $IC_{50}$-value of 8-[(2,6-dimethylbenzyl)amino]-N-(2-hydroxyethyl)-2,3-dimethylimidazo[1,2-a]pyridine-6-carboxamide was measured to 0.75 µmol/l.

2. In vivo Experiments

Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5-4 h (1.2 ml/h, subcutaneously) of pentagastrin and carbachol (20 and 110 nmol/kg·h, respectively), during which time gastric secretions are collected in 30-min fractions. Test substance or vehicle are given either at 60 min after starting the stimulation (intravenous and intraduodenal dosing, 1 mil/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4-6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727-728). The cannulas are exteriorized at the nape of the neck.

Blood samples (0.1-0.4 g) are drawn repeatedly from the carotid artery at intervals up to 5.5 hours after given dose. The samples are frozen until analysis of the test compound.

Bioavailabiity is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F%) following intraduodenal or oral administration is calculated as F(%)= (AUC (p.o. or i.d.)/AUC (i.v.))×100.

Inhibition of Gastric Acid Secretion and Bioavailability in the Conscious Dog.

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80 % of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F%) after oral or i.d. administration is calculated as described above in the rat model.

The effect on histamine-simulated acid secretion of the Heidenhain pouch dog, administered with 0.25 µmol/l of the compound of the invention was determined, the mean percentage inhibition after 1-3 hours (mean, n=2) is 91%.

The bioavailability of 8-[2,6-dimethylbenzyl)amino]-N-(2-hydroxyethyl)-2,3-dimethylimidazo[1,2-a]pyridine-6-carboxamide (0.25 µmol/l) was 61%.

Solubility in Fasted State Simulated Intestinal Fluid (FaSSIF)

The method describes a procedure to measure solubility of solid material in PaSSIF (Fasted State Simulated Intestinal Fluid). The FaSSIF solution is an isotonic phosphate buffer where pH is adjusted to 6.5 to reflect pH in the jejunum. Taurocholic acid and lecithin is added to a concentration of 3 mmol/l and 0.75 mmol/l respectively.

1 mg of solid material, i.e. of the compound of invention, is added to 1 ml FaSSIF solution and equilibrated at 37° C. Samples are withdrawn after 1 and 24 hours. The samples are transferred to eppendorf tubes and spun at 10000 G and 37° C. for 10 minutes. A suitable volume of the supernatant is removed and diluted to a suitable concentration. The concentrations of the compounds in the samples are analysed with LC/UV/MS.

The solubility of the compound of the invention, measured after 24 hours, was 48 μmol/l and the solubility of the compound of the invention as mesylate salt, measured after 24 hours, was 218 μmol/l.

The invention claimed is:

1. A compound of formula I,

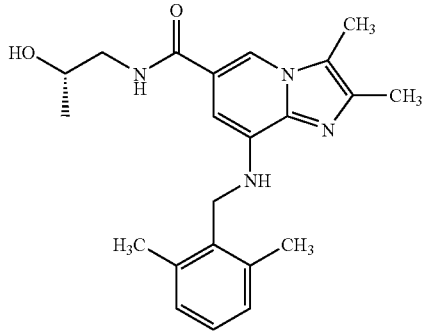

(I)

or a pharmaceutically acceptable salt thereof.

2. The compound according to claim 1, wherein the compound is 8-[(2,6-dimethylbenzyl)amino]-N-[(2S)-2-hydroxypropyl]-2,3-dimethylimidazo[1,2-a]pyridine-6-carboxamide mesylate salt.

3. A pharmaceutical formulation comprising the compound according to claim 1 or 2 as active ingredient in combination with one or more pharmaceutically acceptable diluents or carriers.

4. A method for the treatment or inhibition of a gastric acid related disease, gastrointestinal inflammatory disease, heartburn, symptomatic GERD, erosive esophagitis, peptic ulcer disease, regurgitation, acid reflux disease, or nausea in a patient, the method comprising administering an effective amount of a compound according to claim 1 or 2 to the patient in need thereof.

* * * * *